United States Patent [19]

Pfirrmann

[11] Patent Number: 4,626,536
[45] Date of Patent: Dec. 2, 1986

[54] COMPOSITIONS FOR COMBATTING TOXAEMIA

[75] Inventor: Rolf W. Pfirrmann, Lucerne, Switzerland

[73] Assignee: Ed Geistlich Sohne Ag fur Chemische/Industrie, Lucerne, Switzerland

[21] Appl. No.: 662,887

[22] Filed: Oct. 19, 1984

[30] Foreign Application Priority Data

Oct. 20, 1983 [GB] United Kingdom ............... 8328111

[51] Int. Cl.⁴ .......................................... A61K 31/54
[52] U.S. Cl. ................................................ 514/222
[58] Field of Search ........................ 424/246; 514/222

[56] References Cited

PUBLICATIONS

Chemical Abstracts, 88: 27803t (1978).

*Primary Examiner*—Jerome D. Goldberg
*Attorney, Agent, or Firm*—Bernard, Rothwell & Brown

[57] ABSTRACT

Compounds of formula (I)

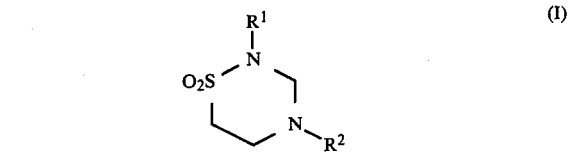

[wherein $R^1$ represents a hydrogen atom or an alkyl group having from 1 to 6 carbon atoms and $R^2$ represents a hydrogen atom, an alkyl group having from 1 to 6 carbon atoms or a group of formula II

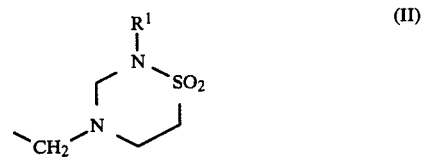

in which $R^1$ is as defined above] and pharmaceutical compositions thereof may be administered to humans or warm-blooded animals to combat toxic proteins or peptides, e.g. venoms, fungal toxins and bacterial exotoxins, in the bloodstream.

4 Claims, No Drawings

COMPOSITIONS FOR COMBATTING TOXAEMIA

This invention relates to compositions comprising methylol transfer antibacterial agents for use in combatting toxaemia caused by toxic proteins and peptides.

Infections caused by Gram-negative bacteria are often characterised by symptoms due to the toxic effects of exotoxins, which are normally proteins substantially free from attached lipopolysaccharide chains. Such exotoxins should be distinguished from endotoxins, which are generally lipopolysaccharides; these are not liberated externally by the intact bacteria although they are commonly released when the invading bacterial cells are destroyed, for example by antibiotics, and may then produce endotoxic shock leading in some cases to fatality. It has been suggested that endotoxaemia could be combatted by admistration of certain methylol-transfer antibacterials such as taurolidine which appear to inactivate the toxins by transfer of methylol or methylene groups. It has never been suggested, however, that toxin proteins such as exotoxins could similarly be inactivated and methylol transfer antibacterials have never been administered parenterally to combat toxic proteins in the absence of lipopolysaccharide toxins.

Although in vitro inactivation of toxic proteins by formaldehyde to produce toxoids has been known for many years, the in vitro deactivation of such toxins by methylol transfer, which requires interaction of the antibacterial substance with the protein at a suitable active site, has not been proposed. Inactivation of lipopolysaccharide endotoxins clearly provides no indication that proteins, i.e. compounds having a completely different chemical structure, could be deactivated. As used herein the term "protein" is restricted to substances consisting substantially entirely of peptide units without attached lipopolysaccharide chains.

According to one aspect of the present invention there are provided for combating toxic proteins or peptides in the bloodstream antibacterial methylol transfer compounds of the general formula (I)

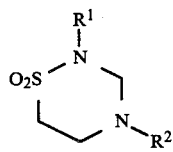

[wherein $R^1$ represents a hydrogen atom or an alkyl group having from 1 to 6 carbon atoms and $R^2$ represents a hydrogen atom, an alkyl group having from 1 to 6 carbon atoms or a group of formula II

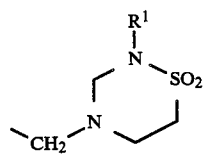

in which $R^1$ is as defined above].

According to another aspect of the invention there is provided a method of treatment of the human or warm-blooded animal body to combat toxic proteins or peptides in the bloodstream, said method comprising administering to said body an effective amount of a compound of formula (I) as defined above.

In the method of the invention, the compounds of formula (I) will conveniently be administered in order to combat toxic proteins or peptides in the substantial absence of bacterial endotoxins. having a completely different chemical structure, could be deactivated. As used herein the term "protein" is restricted to substances consisting substantially entirely of peptide units without attached lipopolysaccharide chains.

According to one aspect of the present invention there are provided for combating toxic proteins or peptides in the bloodstream antibacterial methylol transfer compounds of the general formula (I)

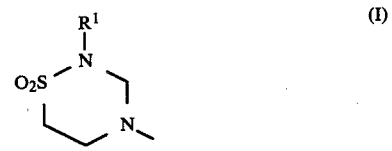

[wherein $R^1$ represents a hydrogen atom or an alkyl group having from 1 to 6 carbon atoms and $R^2$ represents a hydrogen atom, an alkyl group having from 1 to 6 carbon atoms or a group of formula II

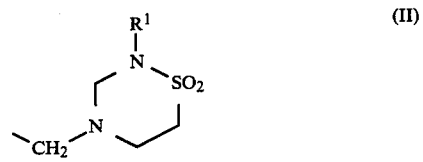

in which $R^1$ is as defined above].

According to another aspect of the invention there is provided a method of treatment of the human or warm-blooded animal body to combat toxic proteins or peptides in the bloodstream, said method comprising administering to said body an effective amount of a compound of formula (I) as defined above.

In the method of the invention, the compounds of formula (I) will conveniently be administered in order to combat toxic proteins or peptides in the substantial absence of bacterial endotoxins.

According to a further aspect of the invention there is provided the use of compounds of formula (I) or pharmaceutical compositions containing as active ingredients compounds of formula (I) for the treatment of the human or warm-blooded animal body to combat toxic proteins or peptides in the bloodstream.

According to a yet further aspect of the invention there is provided a pharmaceutical composition for use in the treatment of the human or warm-blooded animal body to combat toxic proteins or peptides in the bloodstream, said composition comprising an effective amount of a compound of formula (I) together with at least one pharmaceutical carrier or excipient.

In the present invention, of the compounds of formula (I), the compounds taurolidine ($R^1$=H; $R^2$=formula II) and taurultam ($R^1$=$R^2$=H) are particularly preferred. A particular advantage of the compounds of formula (I) is their very low toxicity; thus methylol transfer activity results in the production of taurine which is found naturally in the body and is particularly non-toxic.

A further advantage of taurolidine is its stability in aqueous solution, enabling the solutions to be prepacked and stored over relatively long periods.

Furthermore, it has recently shown to be nonteratogenic in mice.

The compositions of the invention may be in forms suitable for systemic, e.g. oral or, more particularly, parenteral administration. Oral forms include tablets, capsules and fluid compositions such as solutions and suspensions. Parenteral forms include sterile aqueous solutions for injection or infusion. Solutions will commonly contain a solubilising agent such as polyvinylpyrrolidone which helps maintain the active substance in solution and also contributes to the isotonicity of the solution.

The polyvinylpyrrolidone (PVP) is preferably incorporated into the solution, e.g. at a concentration in the range 4 to 7% by weight, in order to achieve relatively high concentrations of taurolidine and the relatively insoluble compounds of formula (I). The molecular weight of the PVP should not be greater than 30,000 and is preferably less than 10,000, for example between 200 and 3500. Kollidone 17 (registered Trade Mark) sold by BASF is especially suitable. Such PVP is relatively quickly resorbed and excreted renally.

The daily dose of the active compound depends, in part, on such factors as the body weight of the subject and the type of toxaemia concerned but in general will be in the range 10 g to 40 g, more preferably 20 g to 30 g per day for therapy and 10 g to 20 g per day, e.g. 15 g, for prophylaxis. Such doses are advantageously given by intravenous infusion. A suitable dosage regime for therapy is four 250 ml bottles per day of 2% solution of the active substance by i.v. drip infusion, with a 4 hour pause. For maintenance 3 such bottles per day may be used, with a 6 hour pause.

The concentration of the substance of formula (I) in such solutions is preferably in the range 0.5 to 5% by weight, depending, at the maximum, on the solubility of the compound. Solutions of 1.0 to 2.0% taurolidine are particularly preferred.

Where the compositions of the invention are in solid form, e.g. as tablets or capsules, they conveniently contain 400 to 700 mg, preferably about 500 mg, of the compound of formula (I). As with iv administered solutions, the daily dosage will depend in part on such factors as the subject's body weight and the type and extent of toxaemia involved; however daily dosages will generally be at least about 10 g, preferably 10 to 30 g.

According to a further aspect the invention provides the use of a compound of formula (I) for the preparation of pharmaceutical compositions for treatment of the human or warm-blooded animal body to combat toxic proteins or peptides in the bloodstream.

According to a still further aspect the invention provides a process for the preparation of pharmaceutical compositions for treatment of the human or warm-blooded animal body to combat toxic proteins or peptides in the bloodstream, said process comprising admixing a compound of formula (I) together with at least one pharmaceutical carrier or excipient.

Toxins which may be concerned include the exotoxins of such Gram-negative bacteria as *E. coli* and *Bacteroides fragilis*. Intravenous administration to mice of 0.2 ml of a 20% solution of taurolidine in sterile 5% polyvinylpyrrolidone very significantly reduced the mortality rate on intraperitoneal administration of pathogenic strains of both *E. coli* and *B. fragilis*.

Other toxic proteins include venoms such as mellitin (bee venom) and fungal toxins such as amanitin and α-bungarotoxin. Our experiments have shown such venoms to be substantially detoxified by taurolidine.

In accordance with the present invention the methylol-transfer antibacterial agent of formula (I) can be administered either therapeutically to combat existing toxaemia or prophylactically to minimize or prevent development of toxaemia symptoms. Prophylactic treatment of subjects with high exposure to toxin sources, such as apiarists, is thus envisaged.

The invention also provides one or more compounds of formula (I) as defined above in association with instructions for use in the method of combating toxaemia according to the invention.

The following non-limiting Examples are provided to illustrate further the present invention:

EXAMPLE 1—SOLUTION

Bis-(1,1-dioxo-perhydro-1,2,4-thiadiazin-4-yl)-methane taurolidine): 400 g Polyvinylpyrrolidone (Kollidone 17): 1000 g Sterile water to: 20 liters 15 Liters double distilled pyrogen free water are filled into a 25 liter glass vessel with stirrer and intensive reflux device and heated to 50° C. with stirring. The taurolidine (400 g) is added followed by PVP (Kollidone 17; 1000 g). After dissolution, the solution is cooled and the pH adjusted to 6.0 with a few drops of 0.1N hydrochloric acid. The solution is then passed through an adsorption filter to remove microorganisms and pyrogens and through a sterilising millipore filter before being filled into 100 ml vials which are finally autoclaved.

EXAMPLE 2—SOLUTION

Taurultam: 990 g

Sterile water ad: 22 liters

The taurultam is dissolved in the sterile water and filled into sterile bottles, 250 ml in each.

EXAMPLE 3—TABLET

Taurolidine: 500 g

Amylum maydis: 60 g

Kollidone 25: 50 g (polyvinylpyrrolidone)

Plasdon XL: 20 g

Magnesium stearate: 6 g

Distilled Water: 200 g 1000 tablets, each containing 500 mg taurolidine, are produced by conventional means using the above formulation.

In an alternative tablet formulation, the amylum maydis is replaced by 60 g amylum orizae.

EXAMPLE 4—SOLUTION

Taurolidine: 440 g

Pharmaceutical gelatin: 88 g

Sodium chloride: 99 g

Sterile water to: 22 liters

The components are dissolved in the sterile water, if necessary using gentle warming and sonication. The solution is then filled into sterile bottles, 500 ml in each.

I claim:

1. A method of treatment of the human or warm-blooded animal body to combat toxic proteins or peptides in the bloodstream, said proteins or peptides being selected from the group consisting of fungal toxins, venoms and bacterial exotoxins, said method comprising administering to said infected body an effective amount for inactivating the toxic proteins or peptides of a compound of formula (I)

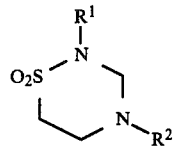 (I)

wherein $R^1$ represents a hydrogen atom or an alkyl group having from 1 to 6 carbon atoms and $R^2$ represents a hydrogen atom, an alkyl group having from 1 to 6 carbon atoms or a group of formula II

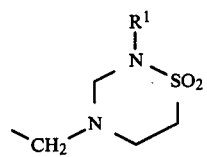 (II)

in which $R^1$ is as defined above.

2. A method as claimed in claim 1 wherein there is administered to said body a compound of formula (I) selected from the group consisting of taurolidine and taurultam.

3. A method as claimed in claim 1 wherein said compound of formula (I) is administered to said body intravenously.

4. A method as claimed in claim 3 wherein from 10 to 40 g of said compound of formula (I) is administered daily.

* * * * *